(12) United States Patent
Suárez et al.

(10) Patent No.: US 8,278,484 B2
(45) Date of Patent: Oct. 2, 2012

(54) PROCESS FOR PREPARING A BENZOYLBENZENEACETAMIDE DERIVATIVE

(75) Inventors: Gabriel Tojo Suárez, A Caruña (ES); Ana Gavaldá Escudé, Barcelona (ES)

(73) Assignee: Medichem, S.A. (ES)

( * ) Notice: Subject to any disclaimer, the term of this patent is extended or adjusted under 35 U.S.C. 154(b) by 211 days.

(21) Appl. No.: 12/483,839

(22) Filed: Jun. 12, 2009

(65) Prior Publication Data

US 2009/0312575 A1   Dec. 17, 2009

Related U.S. Application Data

(60) Provisional application No. 61/061,215, filed on Jun. 13, 2008, provisional application No. 61/117,834, filed on Nov. 25, 2008.

(51) Int. Cl.
C07C 231/12 (2006.01)
C07C 233/05 (2006.01)

(52) U.S. Cl. .................................. 564/162; 564/163

(58) Field of Classification Search .................. 564/162, 564/163

See application file for complete search history.

(56) References Cited

U.S. PATENT DOCUMENTS 4,313,949 A   2/1982   Shanklin, Jr. et al.

OTHER PUBLICATIONS

Walsh et al., *Journal of Medicinal Chemistry*, 33(8): 2296-2304 (1990).

*Primary Examiner* — Shailendra Kumar
(74) *Attorney, Agent, or Firm* — Leydig. Voit & Mayer, Ltd.

(57) ABSTRACT

Disclosed is a process for preparing anti-inflammatory compound nepafenac comprising preparing a compound of formula (V) wherein a N-halosuccinimide is used as the halogenating agent, followed by desulfurization using Raney Nickel. Also disclosed is a polymorphic form B of 2-amino-3-benzoyl-α-(methylthio)-benzeneacetamide (i.e., a compound of formula (V) wherein R is methyl

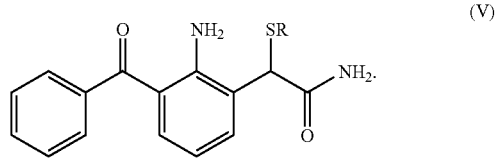

18 Claims, 8 Drawing Sheets

PROCESS FOR PREPARING A BENZOYLBENZENEACETAMIDE DERIVATIVE

CROSS-REFERENCE TO RELATED APPLICATIONS

This patent application claims the benefit of U.S. Provisional Patent Application Nos. 61/061,215 filed Jun. 13, 2008 and 61/117,834 filed Nov. 25, 2008, both of which are incorporated by reference.

BACKGROUND OF THE INVENTION

Nepafenac (compound I) is the international common accepted name for 2-amino-3-benzoylbenzeneacetamide, and has an empirical formula of $C_{15}H_{14}N_2O_2$, and a molecular weight of 254.28 g/mol.

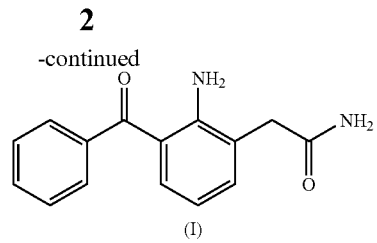

(I)

Nepafenac is a non-steroidal anti-inflammatory active pharmaceutical substance with analgesic activity. In the United States, nepafenac is marketed under the name NEVANAC™, and is indicated for ophthalmic use.

A preparation of nepafenac and similar compounds is disclosed in U.S. Pat. No. 4,313,949 ("the '949 patent"), which is incorporated herein by reference. The '949 patent's method of preparing nepafenac is depicted herein as Scheme 1.

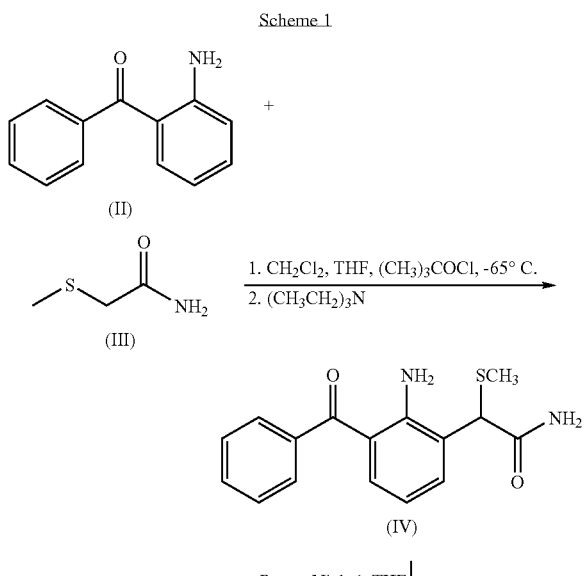

Preparation 7 of the '949 patent describes the production of compound (IV) by using 2-aminobenzophenone (compound of formula II), and methylthioacetamide (compound of formula III), as starting materials, tert-butyl hypochlorite as a chlorinating agent, triethylamine as a base, and a mixture of dichloromethane and tetrahydrofuran as a solvent. The '949 patent makes use of 2-amino-3-benzoyl-α-(methylthio)-benzeneacetamide (compound of formula IV), as an intermediate compound, which is converted into nepafenac (compound I) via desulfurization using Raney nickel as a catalyst as in Example 2.

However, the synthesis of compound (IV) described in the '949 patent suffers from a number of drawbacks. For example, following the teachings of Preparation 7 of the '949 patent (i.e. see Comparative Example 1), the inventors have discovered that several chlorination by-products of compound (II) and compound (IV) (e.g., 2-amino-3-benzoyl-5-chloro-α-(methylthio)benzeneacetamide, 2-amino-3-chlorobenzophenone, and 2-amino-5-chlorobenzophenone) are obtained in considerable amounts. Consequently, the inventors have observed that the preparation described in the '949 patent affords compound (IV) in low yields and with significant amounts of chlorinated by-products, which additionally cause reproducibility problems. Further, the synthesis of compound (IV) disclosed in the '949 patent requires very low temperatures, e.g., about −65° C., which is difficult to achieve at industrial scale and would involve the use of special apparatus. In addition, the chlorinating agent (i.e., tert-butyl hypochlorite) poses a handling hazard as it is unstable, light-sensitive, and decomposes explosively. Accordingly, tert-butyl hypochlorite must be stored at temperatures below 10° C.

In view of the foregoing, there is an unmet need for a reproducible, high-yielding process for preparing compound (IV) which does not produce chlorinated by-products and can be carried out at higher temperatures, wherein said process is suitable for preparing nepafenac in a large scale. There is, therefore, an unmet need for an improved process for preparing the benzoylbenzeneacetamide derivative nepafenac.

BRIEF SUMMARY OF THE INVENTION

The present invention provides an improved process for preparing nepafenac, including nepafenac which is free or substantially free of chlorination by-products.

In an embodiment, the invention provides an improved process for preparing a compound of formula (V):

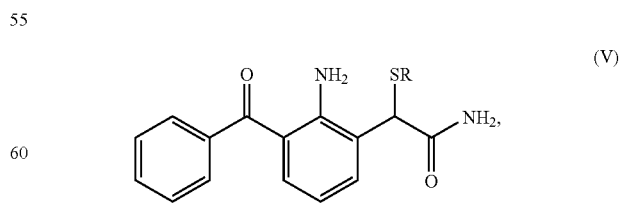

wherein R is described herein.

In another embodiment, the invention provides 2-amino-3-benzoyl-α-(methylthio)-benzeneacetamide of formula (IV) in polymorphic form B:

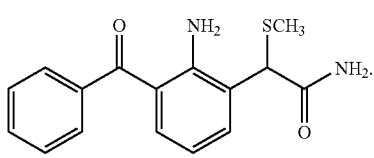

(IV)

In other embodiments, the present invention provides a process for preparing a polymorphic form B of compound (IV).

Processes of the invention have one or more of the following advantages. They are reproducible, high-yielding and/or produce compounds of formula (V), including compound of formula (IV). In keeping with invention, processes of the invention can be carried out at higher temperatures, produce little or no chlorination by-products, and/or are suitable for preparing nepafenac on a large scale.

DETAILED DESCRIPTION OF THE INVENTION

Figure 1:
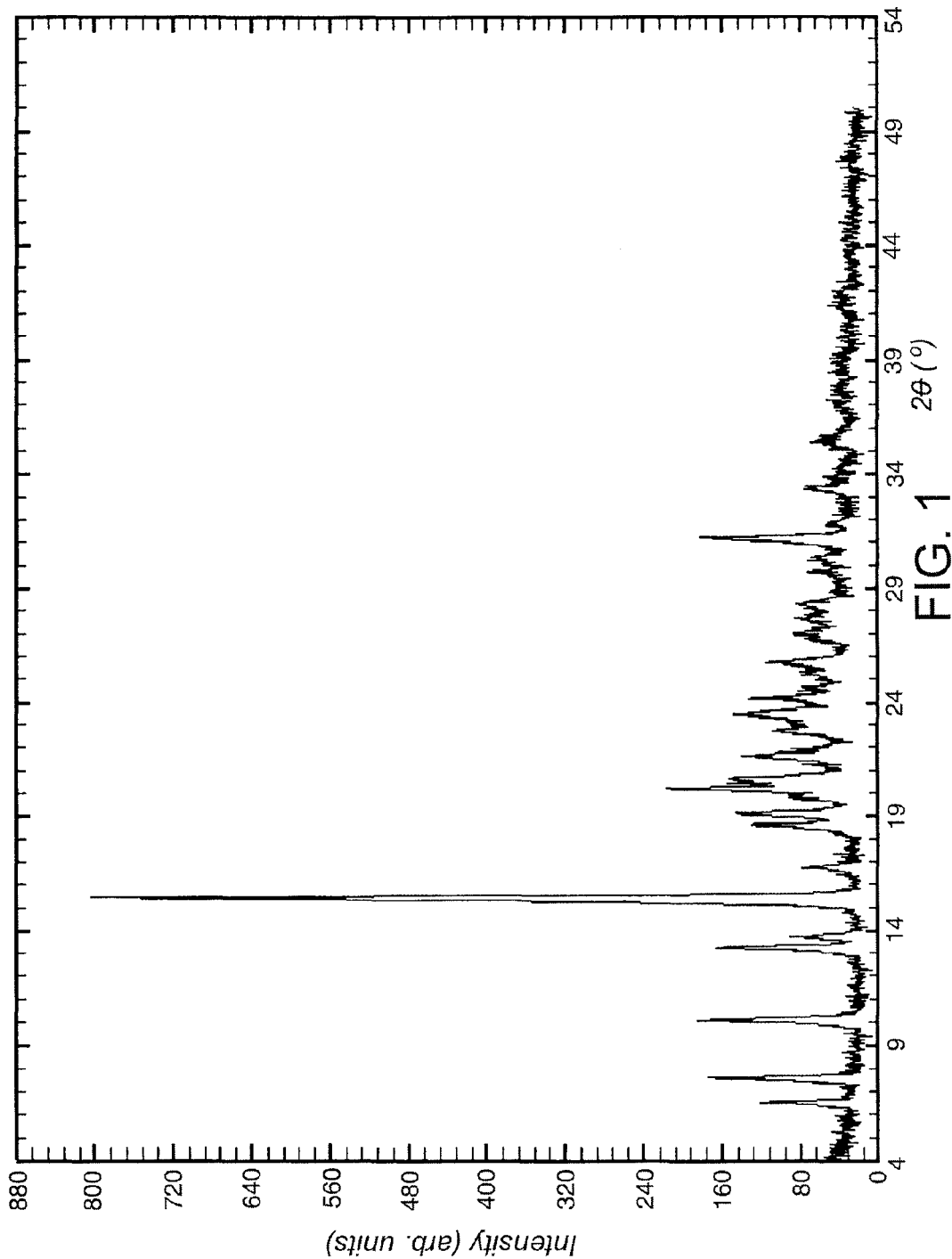
FIG. 1 is an XRD of 2-amino-3-benzoyl-α-(methylthio) benzeneacetamide (i.e., compound of formula (IV) Form A.

In an embodiment, the present invention provides a process for preparing a compound of formula (V):

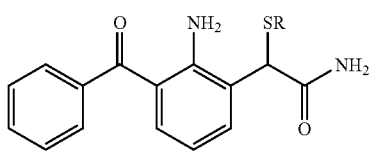

(V)

wherein said process comprises i) reacting a compound of formula (VI):

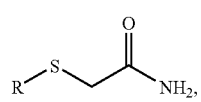

(VI)

with an N-halosuccinimide compound and 2-aminobenzophenone of formula (II):

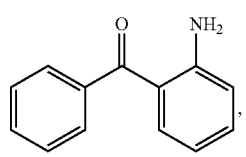

(II)

wherein R is alkyl or aryl, in the presence of an organic solvent, to obtain a reaction mixture; ii) treating the reaction mixture with a base to obtain a mixture comprising compound (V), and iii) optionally, isolating a compound (V) from the mixture.

In accordance with an embodiment, the alkyl group of R can be any suitable alkyl group, e.g., $C_1$-$C_6$ alkyl, preferably $C_1$-$C_3$ alkyl.

In accordance with an embodiment, the aryl group of R can be any suitable aryl group, e.g., $C_6$-$C_{20}$ aryl, such as phenyl, naphthyl, biphenyl, anthracenyl, and the like.

A specific example of a compound of formula (V) is 2-amino-3-benzoyl-α-(methylthio)-benzeneacetamide of formula (IV), that is, a compound of formula (V) wherein R is methyl.

Illustrative compounds of formula (V) include, for example, 2-amino-3-benzoyl-α-(1-propylthio)-benzeneacetamide, 2-amino-3-benzoyl-α-(2-propylthio)-benzeneacetamide, or 2-amino-3-benzoyl-α-(phenylthio)-benzeneacetamide.

Illustrative compounds of formula (VI) include other thioacetamide derivatives known in the art which are suitable to accomplish the reaction such as, for example, 1-propylthioacetamide, 2-propylthioacetamide, or phenylthioacetamide.

A specific example of a compound of formula (VI) is methylthioacetamide of formula (III), that is, a compound of formula (VI) wherein R is methyl.

In an embodiment, the invention provides relates to an improved process for preparing 2-amino-3-benzoyl-α-(methylthio)-benzeneacetamide (compound of formula IV), which does not give chlorinated by-products, which affords compound (IV) with good yields, which is very reproducible, which is carried out at a temperature greater than or equal to about −40° C., and/or which is useful for preparing nepafenac in a large scale.

In an embodiment, the present invention provides a process for preparing 2-amino-3-benzoyl-α-(methylthio)-benzeneacetamide (compound of formula IV), said process comprising (i) reacting methylthioacetamide (compound of formula III), with an N-halosuccinimide compound such as N-chlorosuccinimide, and 2-aminobenzophenone (compound of formula II), in the presence of dichloromethane or other suitable organic solvent, and at a temperature greater than or equal to about −40° C., to obtain a mixture; (ii) treating the mixture with a base to obtain a mixture comprising compound (IV); and (iii) optionally, isolating compound (IV) from the mixture.

In certain embodiments, the compound (VI) of step i) of the process of the invention is methylthioacetamide (i.e., compound III), and therefore the compound of formula (V) is 2-amino-3-benzoyl-α-(methylthio)-benzeneacetamide (i.e., compound (IV)).

In an alternative embodiment, the compound (VI) is 2-propylthioacetamide, and hence the compound of formula (V) is 2-amino-3-benzoyl-α-(2-propylthio)-benzeneacetamide.

A suitable organic solvent to conduct the process of the invention step i) is preferably acetonitrile. More preferably, the organic solvent of the process of the invention is anhydrous acetonitrile. It has been observed by the present inventors that acetonitrile is a preferred suitable solvent for carrying out the reaction as it shows a high solubility power and so can be used in reduced volumes as compared with the prior art. In addition, it has been observed that the reaction is more efficiently conducted in the absence of water. So, the solvents of the process of the process of the invention are preferably anhydrous solvents.

The temperature greater than or equal to about −40° C. of step i) of the process of the invention is preferably between about −30 to 0° C., and more preferably is about −25° C. The inventors have surprisingly observed that by carrying out the process of the invention, i.e. using an N-halosuccinimide instead of tert-butyl hypochlorite as compared with the prior art, the reaction of step i) of the process of the invention is not only safer, but can be surprisingly conducted at a temperature of at least 25° C. higher, preferably at least 40° C. higher, than the temperature of the corresponding step described in the prior art (i.e., −65° C.).

The base used in step ii) of the process of the invention is preferably an organic base. More preferably, the base used in step (ii) of the process of the invention is a trialkylamine or an aryldialkylamine, and even more preferably is triethylamine.

The process of the invention preferably comprises the steps of i) preparing a mixture of compound of formula (VI) and compound of formula (II) in a suitable organic solvent; ii) adding an N-halosuccinimide compound such as N-chlorosuccinimide to the mixture at a temperature greater than or equal to about −40° C.; iii) maintaining the reaction mixture at a temperature greater than or equal to about −40° C. for a suitable period of time; iv) adding a base to the reaction mixture; and v) isolating compound of formula (IV) from the mixture.

In another aspect, the present inventors have surprisingly observed that by selecting a suitable organic solvent, the process of the present invention can afford compound (IV) in different crystalline forms (i.e. known Form A, or new Form B). Namely, when the organic solvent of step i) of the process of the invention is dichloromethane, the compound (IV) isolated in step (iii) of the process of the invention is compound (IV) in known polymorphic Form A. Conversely, when the organic solvent of step i) of the process of the invention is acetonitrile, the mixture comprising compound (IV) of step ii) of the process of the invention is surprisingly a suspension comprising compound (IV) in a new polymorphic form (from now, Form B).

In a further aspect, the inventors have surprisingly found that compound (IV) new Form B shows improved and unexpected properties as compared with known Form A, which are especially advantageous for the isolation step iii) of the process of the invention.

Specifically, compound (IV) known Form A shows a good solubility profile in the reaction mixture, which typically implies that the isolating compound (IV) in known Form A of step iii) of the process of the invention comprises removing the solvent from the solution, for example by evaporating the solvent. Conversely, compound (IV) Form B shows a low solubility profile in the reaction mixture of the process of the invention (i.e. solubility in acetonitrile=approx. 5.9 mg/mL) and so precipitates when produced, which hence implies that compound (IV) Form B can be easily isolated from the reaction mixture by simply filtering the suspension. Optionally, water can be added to the suspension earlier than the filtration. Further, this filtration step introduces an additional purification step.

In addition, the lower solubility profile of compound (IV) Form B has no unfavourable effect in the later step of the preparation of nepafenac which is typically carried out in tetrahydrofuran or in mixtures of tetrahydrofuran and water, as compared to compound (IV) known Form A. The present inventors have calculated the solubility profile at room temperature of both compound (IV) known Form A and new Form B, and have confirmed that both are soluble in tetrahydrofuran (i.e. Form A solubility=approx. 50 mg/mL; Form B solubility=approx. 33 mg/mL) and in a 1:1 mixture of tetrahydrofuran/water (i.e. Form A solubility=approx. 50 mg/mL; Form B solubility=approx. 50 mg/mL).

In a preferred embodiment of the invention, the process for preparing compound of formula (IV) comprises i) preparing a mixture of compound of formula (III) and compound of formula (II) in anhydrous acetonitrile, ii) adding N-chlorosuccinimide to the mixture at a temperature of about −25° C., iii) maintaining the reaction mixture at a temperature of about −25° C. for a suitable period of time; iv) adding triethylamine to the reaction mixture, to obtain a suspension comprising compound (IV) in new polymorphic Form B; and v) isolating compound of formula (IV) Form B by filtering the suspension.

A compound of Formula (IV) obtained according to the process of the invention can be purified by slurrying or crystallization methods, thereby obtaining compound of Formula (IV) in different crystalline forms (i.e. known Form A, new Form B, or mixtures thereof).

In an embodiment, the compound of Formula (IV) is purified by slurrying in a suitable solvent, thereby obtaining compound of Formula (IV) in crystalline Form A. The suitable solvent preferably is selected from the group consisting of diethyl ether, methyl tert-butyl ether, and mixtures thereof.

In an embodiment, the compound of Formula (IV) is purified by crystallization in a suitable solvent, thereby obtaining compound of Formula (IV) in crystalline Form A. A suitable solvent preferably is 2-propanol.

In an embodiment, the compound of Formula (IV) is purified by slurrying in a suitable solvent, thereby obtaining compound of Formula (IV) in a new crystalline form (denominated herein as Form B). The suitable solvent preferably is selected from the group consisting of water and mixtures of water and acetonitrile.

In an embodiment, the compound of Formula (IV) is purified by crystallization in a suitable solvent, thereby obtaining compound of Formula (IV) in new crystalline Form B. A suitable solvent preferably is methyl isobutyl ketone.

In an embodiment, the compound of Formula (IV) is purified by crystallization in a suitable solvent, thereby obtaining compound of Formula (IV) in a mixture of crystalline Forms A and B. A suitable solvent preferably is selected from the group consisting of acetonitrile, ethyl acetate, isopropyl acetate, methyl ethyl ketone, methanol, and mixtures thereof.

In accordance with another aspect of the invention, the present invention provides a novel polymorphic form of 2-amino-3-benzoyl-α-(methylthio)-benzeneacetamide (compound of formula (IV)). This form has been prepared and characterized herein by its X-ray powder diffraction pattern (XRD), its Differential Scanning Calorimetry (DSC) thermogram, and its IR spectrum, and is referred to herein as Form B.

Figure 3:
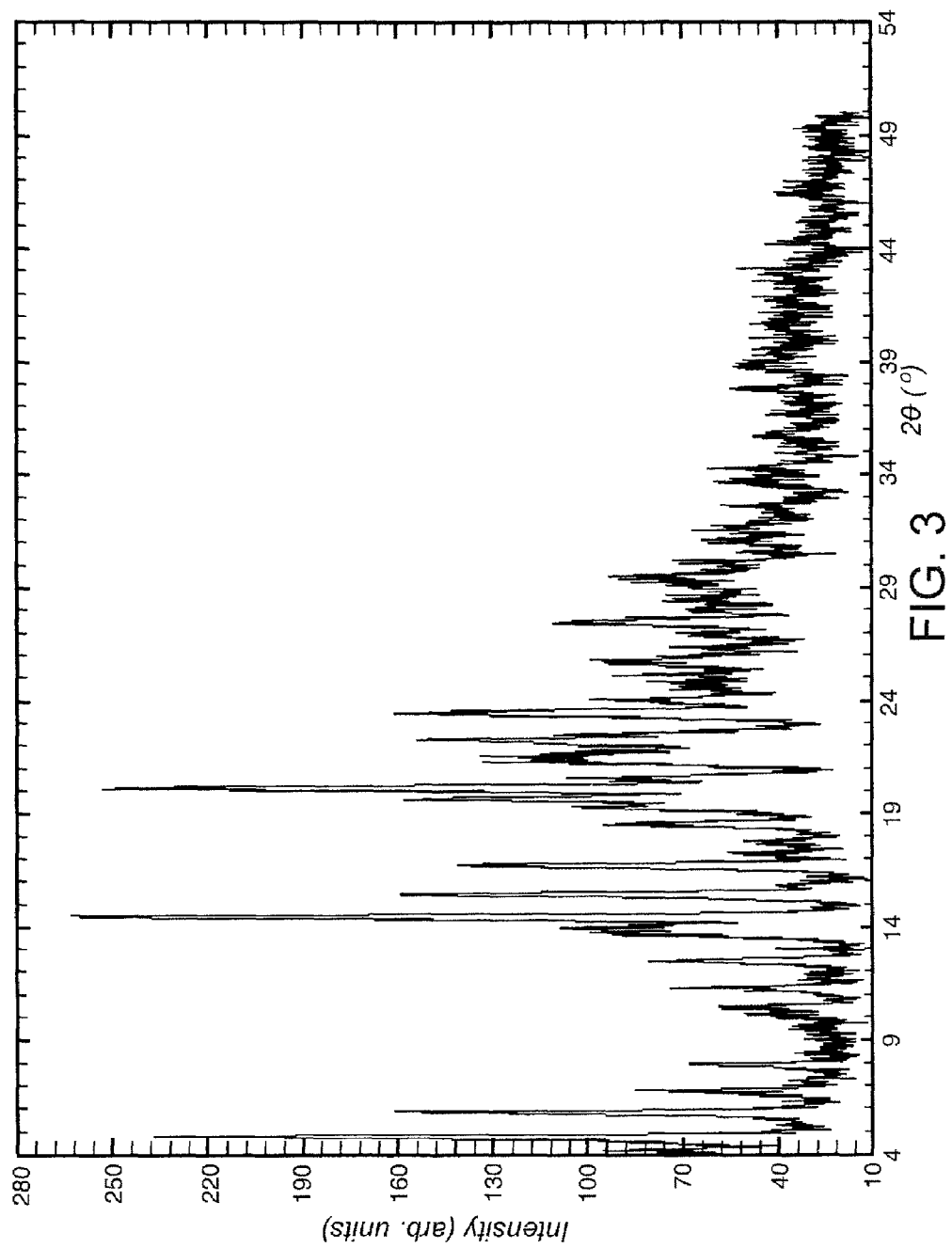
FIG. 3 is an XRD of 2-amino-3-benzoyl-α-(methylthio) benzeneacetamide of formula (IV) Form B.

FIG. 3 illustrates the X-ray powder diffraction pattern (2θ) (±0.2°) of compound of formula (IV) Form B which has its main peaks at approximately 4.2, 4.8, 5.9, 6.8, 7.9, 10.4, 11.3, 12.5, 13.7, 13.9, 14.4, 15.4, 16.7, 17.2, 17.7, 18.5, 19.2, 19.6, 20.1, 20.6, 21.3, 21.5, 22.2, 23.4, 24.0, 25.1, 25.7, 26.3, 26.9, 27.5, 29.5, 30.1, 32.6, 34.3, 35.8, 37.8.

Figure 8:
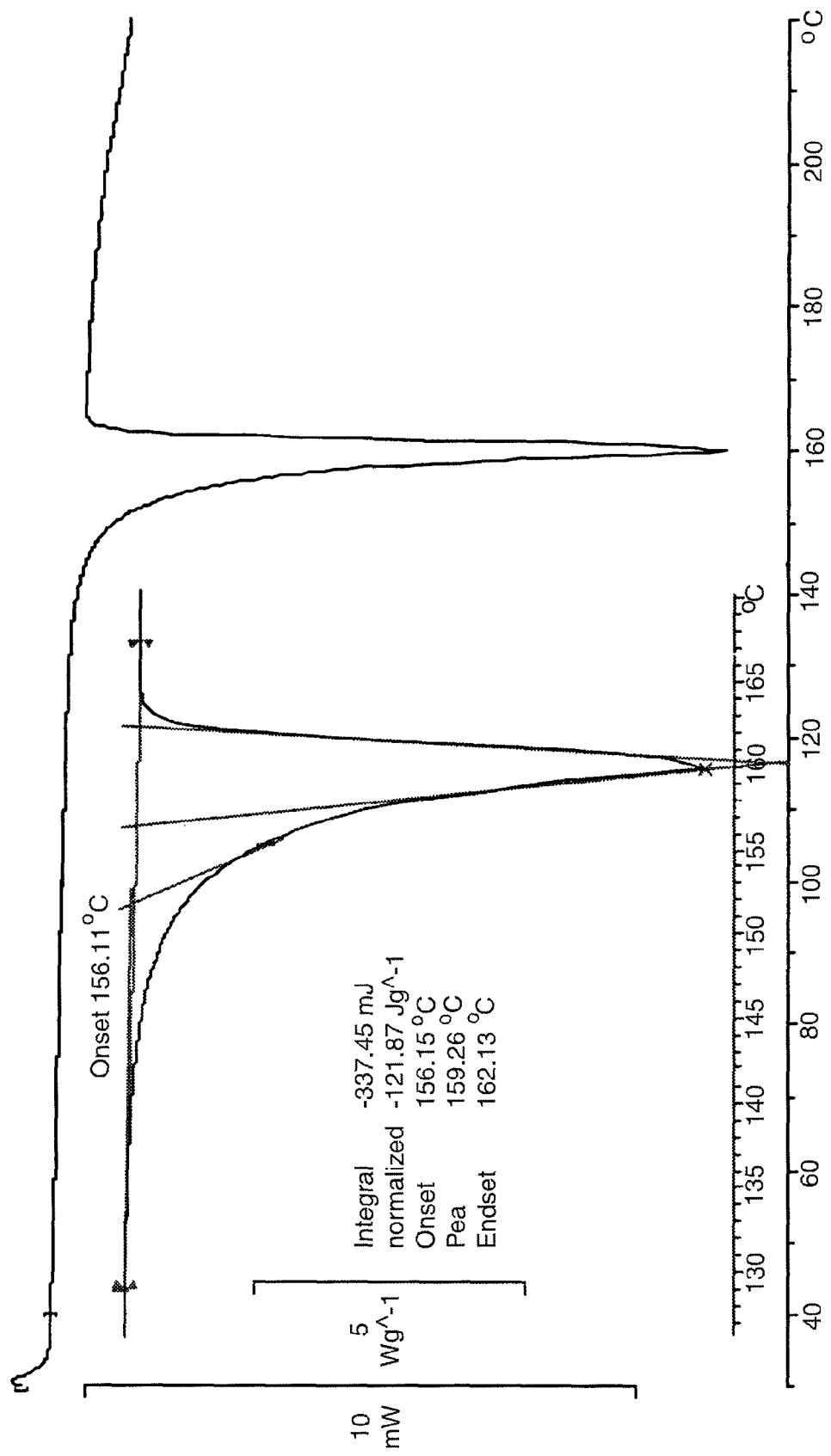
FIG. 8 is a DSC thermogram of 2-amino-3-(methylthio)benzeneacetamide of formula (IV) Form B.

The compound of formula (IV) polymorphic Form B of the invention shows a DSC thermogram obtained in an open pan having an endothermic peak at approximately 159.3° C. with an onset of a transition at 156.2° C. (See FIG. 8).

In another embodiment, the compound of formula (V) obtained according to the process of the invention (e.g. compound (IV) Form B) is used for preparing nepafenac.

In yet another embodiment, the invention provides a process for preparing nepafenac, said process comprising (iv) reacting the compound of formula (V) obtained according to the process of the invention with Raney nickel, and in the presence of a suitable solvent; (v) isolating nepafenac from the reaction mixture; vi) optionally, recrystallizing nepafenac in a suitable solvent such as 2-propanol; vii) optionally, treating nepafenac with at least one metal scavenger such as SMOPEX®; and viii) optionally, reducing the particle size of nepafenac by conventional techniques such as grinding, crushing, or milling.

The reaction of step v) of the process above is preferably performed in a filter reactor. The use of a filter reactor allows reducing the hazards associated with Raney nickel and facilitates the washings of Raney nickel which are required prior to its use in the reaction process.

The suitable solvent of step iv) of the process above is preferably selected from the group consisting of tetrahydrofuran and mixtures of tetrahydrofuran and water.

The process of the present invention provides compound of formula (IV) having less than or equal to 0.5% of 2-amino-3-benzoyl-5-chloro-α-(methylthio)benzeneacetamide, preferably having less than or equal to 0.1%, and more preferably having less than or equal to 0.01%.

The process of the present invention provides compound of formula (IV) having less than or equal to 0.5% of 2-amino-3-chlorobenzophenone, preferably having less than or equal to 0.1%, and more preferably having less than or equal to 0.01%.

The process of the present invention provides compound of formula (IV) having less than or equal to 0.5% of 2-amino-5-chlorobenzophenone, preferably having less than or equal to 0.1%, and more preferably having less than or equal to 0.01%.

In a preferred embodiment, the process of the present invention provides a compound of formula (IV) having less than or equal to 0.5% 2-amino-3-benzoyl-5-chloro-α-(methylthio)benzeneacetamide, less than or equal to 0.1% 2-amino-5-chlorobenzophenone, and less than or equal to 0.1% 2-amino-3-chlorobenzophenone.

In a further preferred embodiment, the process of the present invention provides a compound of formula (IV) having less than or equal to 0.1% 2-amino-3-benzoyl-5-chloro-α-(methylthio)benzeneacetamide, less than or equal to 0.1% 2-amino-5-chlorobenzophenone, and less than or equal to 0.1% 2-amino-3-chlorobenzophenone.

In a further preferred embodiment, the process of the present invention provides a compound of formula (IV) having less than or equal to 0.01% 2-amino-3-benzoyl-5-chloro-α-(methylthio)benzeneacetamide, less than or equal to 0.01% 2-amino-5-chlorobenzophenone, and less than or equal to 0.01% 2-amino-3-chlorobenzophenone.

The nepafenac obtained by the process above is free or substantially free of compound (II) and compound (IV) chlorination by-products.

Another aspect of the invention includes a pharmaceutical composition including nepafenac obtained according to the process of the invention. Pharmaceutical compositions in accordance with the invention comprise a pharmaceutical carrier as appropriate.

The following examples further illustrate the invention but, of course, should be construed as in any way limiting its scope.

General Experimental Conditions.

HPLC method. The chromatographic separation was carried out in a Waters Sunfire C18, 5 μm 4.6×150 mm column. The mobile phase A was a 10 mM ammonium formate buffer pH=4.0, which was prepared from 0.63 g of $HCOONH_4$ dissolved in 1000 mL of water adjusting the pH to 4.0 with formic acid. This mobile phase was mixed and filtered through a 0.22 μm nylon membrane under vacuum. The mobile phase B was acetonitrile.

The chromatograph was programmed as follows: Initial 0-30 min. 70% mobile phase A, 30-35 min. linear gradient to 60% mobile phase A, 35-150 min. isocratic 60% mobile phase A, 150-155 min. linear gradient to 70% mobile phase A and 155-160 min. equilibration with 70% mobile phase A.

The chromatograph was equipped with a 245 nm detector and the flow rate was 1.0 mL per minute at 30° C. Test samples were prepared by dissolving 25 mg of sample in 50 mL of acetonitrile, and 10 μl were injected.

GC Method. The GC analysis was performed on an Agilent 6890N. The following parameters were used: Gas carrier: He; Column head pressure: 7 psi; Split ratio: 25:1, Injector Temp.: 250° C.; Detector Temp. (FID): 300° C.; Column: TRB-5A (5% phenyl, 95% dimethylpolisiloxane), 30 m length, 0.32 mm internal diameter, 0.5 μm film thickness. The following temperature program was used: Initial Temp.: 90° C.; Initial time: 5 min; Rate 1: 10° C./min; Final Temp. 1: 200° C.; Final time 1: 10 min, Rate 2: 20° C./min; Final Temp. 2: 280° C.; Final time 2: 15 min; Injection volume: 2 μL (Agilent 7683 autosampler). Sample preparation: the sample was dissolved in methanol to a concentration of 20 mg/mL.

X-ray Powder Diffraction (XRD). The XRD diffractograms were obtained using a RX SIEMENS D5000 diffractometer with a vertical goniometer, a copper anodic tube, and radiation $CuK_\alpha$, $\lambda$=1, 54056 Å.

Infrared Spectr$_a$ (IR). Fourier transform IR spectra were acquired on a Thermo Nicolet Nexus spectrometer, and polymorphs were characterized in potassium bromide pellets.

SPECIFIC EXAMPLES

Comparative Example 1

Preparation of 2-amino-3-benzoyl-α-(methylthio) benzeneacetamide (i.e. compound of formula IV)

This example was carried out following the teachings of Preparation 7 of U.S. Pat. No. 4,313,949.

1.01 g (5.14 mmol) of 2-aminobenzophenone was dissolved in 15 mL of anhydrous dichloromethane (refluxed with $P_2O_5$) under inert atmosphere. The resulting solution was cooled to −70° C. in a dry-ice/acetone cooling bath. 0.56 g (5.16 mmol) of tert-butyl hypochlorite freshly prepared were added within 5 min.

The resulting suspension was stirred at −70° C. for 30 min. A solution of 0.45 g (4.28 mmol) of methylthioacetamide in 15 mL of anhydrous THF (refluxed with Na) was added within 20 min., controlling the temperature below −60° C. A solution was typically obtained after the addition. The reaction mixture was allowed to warm to 15° C. within 1 h. A yellow-green solid precipitated off during the warming. The reaction mixture was cooled again to −70° C. 0.54 g (5.34 mmol) of triethylamine was added dropwise. A solution was obtained. The reaction mixture was allowed to warm to room temperature within 1 h and was then extracted with 2×10 mL of $H_2O$. The organic layer was dried over anhydrous $Na_2SO_4$, filtered and evaporated to dryness. 1.07 g of a yellow solid was obtained. The solid was slurried with 10 mL of diethyl ether, stirred at room temperature for 10 min and then filtered. The cake was washed with 5 mL of diethyl ether. 0.52 g of a yellow solid was obtained. (Yield: 40%).

Figure 2:
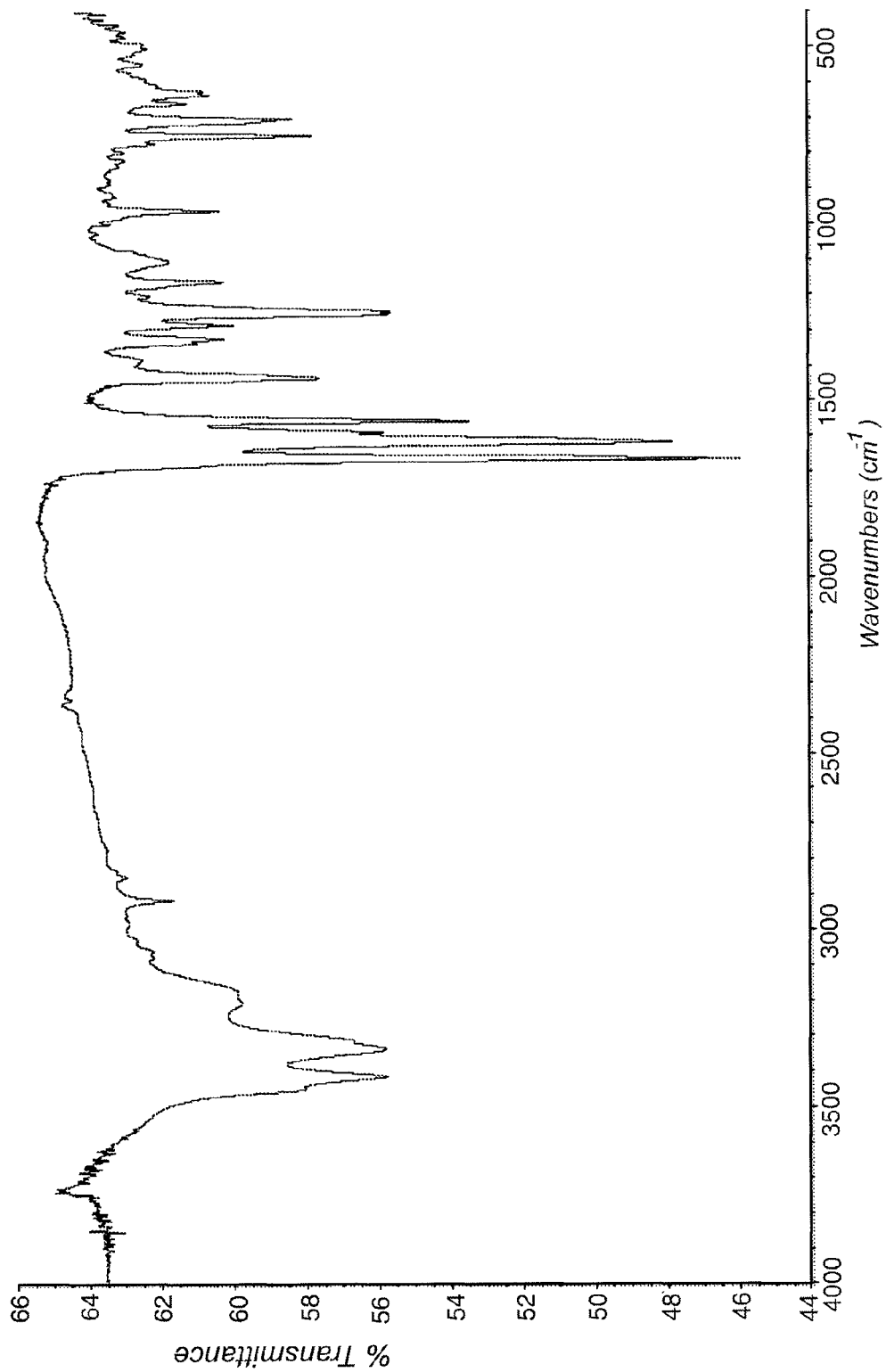
FIG. 2 is an IR spectrum of 2-amino-3-benzoyl-α-(methylthio)benzeneacetamide of formula (IV) Form A.

Analytical data: HPLC purity: 84%; Chlorination by-products observed by HPLC: 2-amino-3-benzoyl-5-chloro-α-(methylthio)benzeneacetamide: 7.62%; 2-amino-5-chlorobenzophenone: 1.19%; 2-amino-3-chlorobenzophenone: 0.12%; XRD: Form A, see FIG. 1; IR, see FIG. 2.

The crystalline form of compound of formula (IV) obtained following the teachings of Preparation 7 of the '949 patent has been characterized herein by X-ray powder diffraction (XRD), and infrared (IR) spectra, and has been denominated herein as Form A.

Comparative Example 2

Preparation of 2-amino-3-benzoyl-α-(methylthio) benzeneacetamide (i.e. compound of formula IV)

This example was carried out following the teachings of Preparation 7 of U.S. Pat. No. 4,313,949 in a larger scale than Comparative Example 1.

To a cold solution (−70° C.) of 19.7 g (0.1 mol) of 2-aminobenzophenone in 300 mL of anhydrous dichloromethane, under inert atmosphere, was added a solution of 11.4 g of freshly prepared tert-butyl hypochlorite in 30 mL of anhydrous dichloromethane, followed after 10 minutes by the addition of a solution of 10.5 g (0.1 mol) of methylthioacetamide in 300 mL of anhydrous tetrahydrofuran. The temperature was maintained at or below −55° C. during these additions. After 1 h at −60° C., the mixture was allowed to warm to 0° C. and 11.2 g of triethylamine was added between 0 and 5° C. The reaction mixture was allowed to warm to ambient temperature and the yellow-orange solution was washed twice with 100 mL of water. The organic phase was dried over sodium sulphate and concentrated. The oily residue was treated with diethyl ether and the resulting solid was collected by filtration and dried to yield 10.2 g as a light yellow powder (Yield: 34%).

Analytical data: HPLC purity: 62%; Chlorination by-products observed by HPLC: 2-amino-3-benzoyl-5-chloro-α-(methylthio)benzeneacetamide: 25.4%; 2-amino-5-chlorobenzophenone: 7.8%; 2-amino-3-chlorobenzophenone: 1.1%.

The foregoing shows that the purity of compound (IV) decreases with scale of the preparation.

Example 1

Preparation of 2-amino-3-benzoyl-α-(methylthio) benzeneacetamide (i.e. compound of formula IV)

This example illustrates the preparation of compound (IV) according to an embodiment of the invention.

A slurry of 2.63 g (25.01 mmol) of methylthioacetamide in 50 mL of anhydrous dichloromethane (refluxed with $P_2O_5$), under inert atmosphere, was cooled to −45° C. with a MeCN/dry ice cooling bath. A solution of 3.41 g (25.03 mmol) of N-chlorosuccinimide in 50 mL of anhydrous dichloromethane was added dropwise, controlling the temperature below −40° C. The resulting suspension was stirred at −45° C. for 30 min. A solution of 4.93 g (24.99 mmol) of 2-aminobenzophenone in 50 mL of anhydrous dichloromethane was added dropwise, controlling the temperature below −40° C. The resulting suspension was stirred at −45° C. for 30 min. The reaction mixture was allowed to warm to 0-8° C. within 1 h 30 min and 2.77 g (27.34 mmol) of triethylamine was added. The reaction mixture became a solution and was extracted with 3×50 mL of $H_2O$. The organic layer was dried over anhydrous $Na_2SO_4$, filtered and evaporated to dryness to give a yellow solid.

Purification: The solid was slurried with 140 mL of diethyl ether, stirred at room temperature for 1 h and then filtered. The resulting cake was washed with 50 mL of diethyl ether.

The purification step was repeated.

6.48 g of a pale yellow solid was obtained (Yield: 86.4%).

Analytical data: HPLC purity: 99.74%; No chlorination by-products were observed by HPLC; XRD: Form A, see FIG. 1.

Example 2

Preparation of 2-amino-3-benzoylbenzeneacetamide (i.e. nepafenac, compound of formula I)

This example illustrates the use of the compound (IV) obtained according to an embodiment of the process of the invention, for preparing nepafenac.

Five teaspoonful (approx. 15 g) of wet Raney-Ni catalyst was loaded (a level teaspoonful is about 3 g. of nickel, see *Organic Syntheses, Coll.* 1955, 3, 181). The catalyst was washed thrice with water and thrice with THF. A solution of 3.00 g of 2-amino-3-benzoyl-α-(methylthio)benzeneacetamide (obtained in Example 1) in 60 mL of THF was loaded. The reaction mixture was vigorously stirred at room temperature for 10 min. An in-process control by TLC was carried out to check that there was no remaining starting material. The reaction mixture was filtered through a Büchner funnel with a Celite® pre-coat in order to remove the catalyst. The resulting cake was washed with 150 mL of THF. The filtrate (yellow solution) was evaporated to dryness in a rotary evaporator to give 2.33 g of a yellow solid. (0.05 g is kept as a sample for HPLC). This solid obtained was slurried in 99 mL of 2-propanol. The slurry was heated to reflux and became a clear solution. The resulting solution was then slowly cooled to 0-5° C. with a water/ice cooling bath and stirred at this temperature for 30 min. During the cooling process a yellow solid precipitated. The solid was collected by filtration in vacuum through a Büchner funnel. The cake was washed with 10 mL of 2-propanol and dried overnight in vacuum at 40° C. 2.05 g of a yellow solid (needles) was obtained (Overall yield: 82.48%).

Analytical data: HPLC purity: 99.5% before the purification, 99.7% after the purification; No chlorination by-products were observed by HPLC.

Example 3

Preparation of 2-amino-3-benzoyl-α-(methylthio) benzeneacetamide (i.e. compound of formula IV)

This example further illustrates the preparation of compound (IV) according to an embodiment of the invention.

85.0 g (0.43 mol) of 2-aminobenzophenone and 45.3 g (0.43 mol) of 2-methylthioacetamide were suspended, under inert atmosphere, in 1175 mL of anhydrous acetonitrile. The resulting suspension was cooled to −25° C. and a solution of 57.6 g (0.42 mol) of N-chlorosuccinimide in 390 mL of acetonitrile was added dropwise at such a rate that the temperature did not exceed −23° C. The reaction mixture was stirred at −25° C. during 30 minutes and it was allowed to warm to 0° C. within 2 h. Then, 66.1 mL (0.47 mol) of triethylamine were added dropwise maintaining the temperature between 0° C. and 5° C. The resulting suspension was allowed to warm to room temperature within 1 h (At this stage, a sample of the wet solid was analyzed by XRD, and was found to correspond to compound (IV) Form B) and 2.0 L of water were added in one portion. The mixture was stirred for 1 hour and the solid was collected by filtration. The solid was slurried again in 660 mL of water at room temperature during 1 hour, filtered and dried to yield 100.7 g as a light yellow powder (Yield: 78%).

Figure 4:
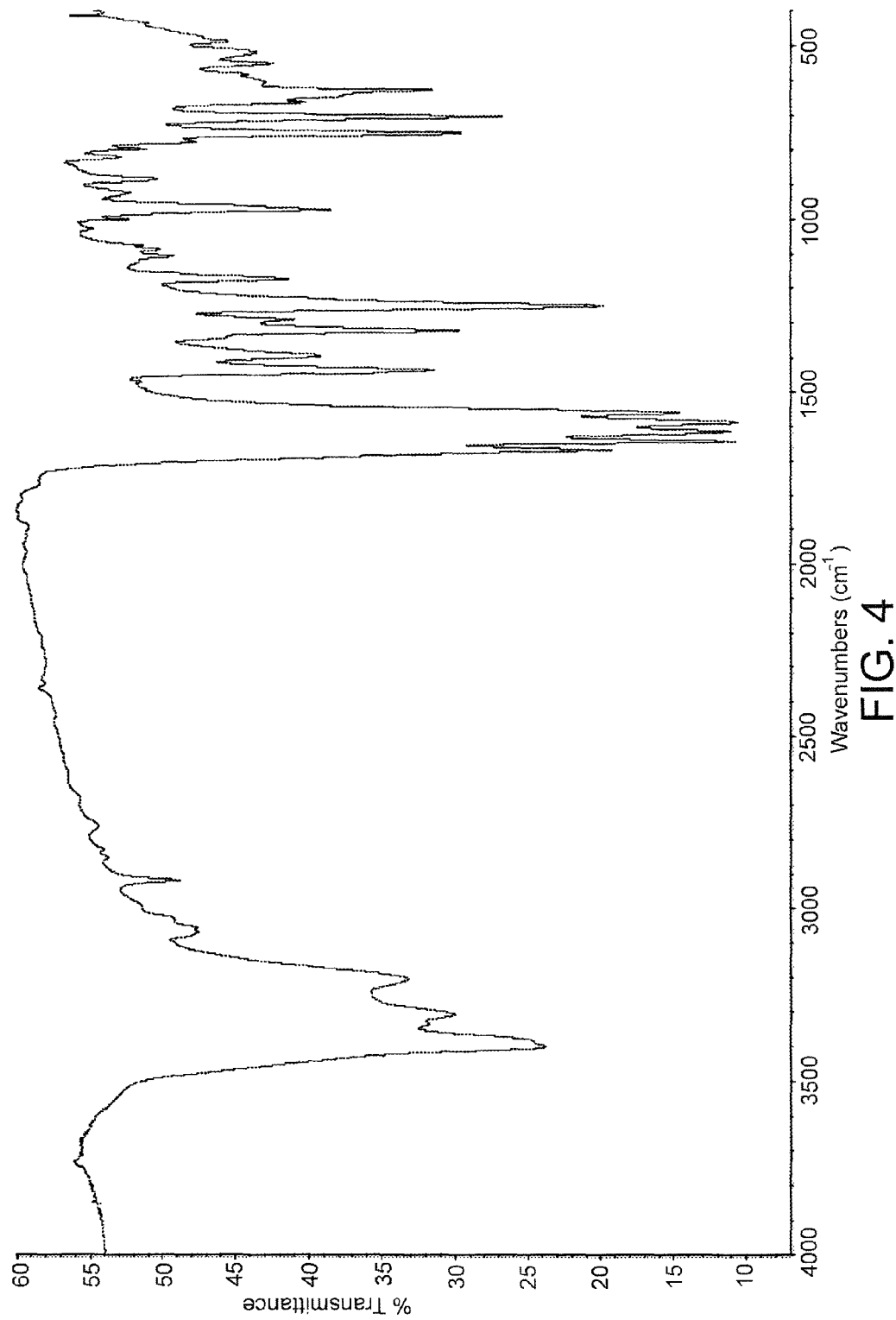
FIG. 4 is an IR spectrum of 2-amino-3-benzoyl-α-(methylthio)benzeneacetamide of formula (IV) Form B.

Analytical data: HPLC purity: 97.2%; 2.5% of 2-aminobenzophenone (compound of formula II) was observed; No chlorination by-products were observed by HPLC; XRD: Form B, see FIG. 3; IR: see FIG. 4.

Example 4

Preparation of 2-amino-3-benzoyl-α-(methylthio) benzeneacetamide (i.e. compound of formula IV) Form A This example illustrates the preparation of compound (IV) Form A by crystallization.

510 mg of 2-amino-3-benzoyl-α-(methylthio)benzeneacetamide was suspended in 12 mL of 2-propanol, and heated to reflux until complete dissolution. The solution was allowed to cool to ambient temperature, filtered and dried.

Figure 7:
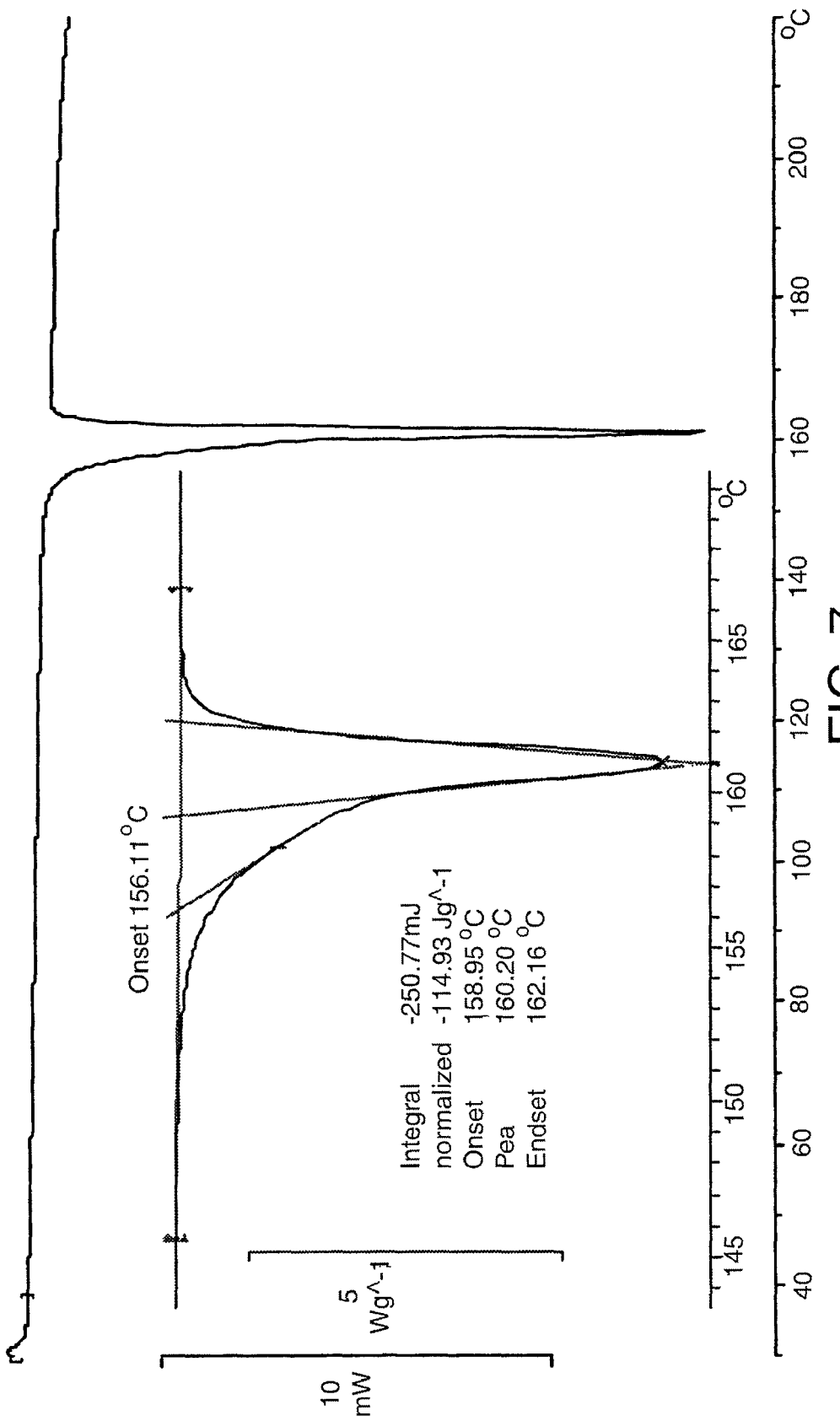
FIG. 7 is a Differential Scanning Calorimetry (DSC) thermogram of 2-amino-3-benzoyl-α-(methylthio)benzeneacetamide of formula (IV) Form A.

Analytical data: XRD: Form A, see FIG. 1; IR: see FIG. 2; DSC: see FIG. 7. Analytical data of the compound after one year at room temperature and ambient atmosphere conditions (XRD and IR): Form A.

Example 5

Preparation of 2-amino-3-benzoyl-α-(methylthio) benzeneacetamide (i.e. compound of formula IV) Form B This example illustrates the preparation of compound (IV) Form B by crystallization.

530 mg of 2-amino-3-benzoyl-α-(methylthio)benzeneacetamide was suspended in 3 mL of methyl isobutyl ketone, and heated to reflux until complete dissolution. The solution was allowed to cool to ambient temperature, filtered and dried.

Analytical data: XRD: Form B, see FIG. 3; DSC: see FIG. 8. Analytical data of the compound after one year at room temperature and ambient atmosphere conditions (XRD and IR): Form B.

Examples 6-10

Preparation of 2-amino-3-benzoyl-α-(methylthio) benzeneacetamide (i.e. compound of formula IV) mixtures of Form A and B This example illustrates the preparation of compound (IV) mixtures of Form A and B by crystallization.

General procedure: 2-amino-3-benzoyl-α-(methylthio) benzeneacetamide was suspended in the solvent and heated to reflux until complete dissolution. The solution was allowed to cool to ambient temperature, filtered and dried. The conditions and the obtained results are described in Table 1 below.

| Example | Quantity | Solvent | Solvent quantity | XRD |
|---|---|---|---|---|
| 6 | 530 mg | Acetonitrile | 9 mL | Form A (traces Form B are observed) |
| 7 | 500 mg | Ethyl acetate | 14 mL | Mixtures Form B and Form A |
| 8 | 510 mg | Isopropyl acetate | 17 mL | Mixtures Form B and Form A |
| 9 | 510 mg | Methyl ethyl ketone | 5 mL | Mixtures Form B and Form A |
| 10 | 540 mg | Methanol | 10 mL | Mixtures Form B and Form A |

Example 11

Preparation of 2-amino-3-benzoylbenzeneacetamide (i.e. nepafenac, compound of formula I)

This example illustrates the use of the compound (IV) Form B obtained according to the process of the invention, for preparing nepafenac.

100 g of wet Raney-Ni catalyst was loaded in the filter reactor and purged with nitrogen or argon. The catalyst was washed twice with water and once with THF (the washings were done opening the bottom valve and applying argon or nitrogen pressure in the reactor). Then 25.0 g of 2-amino-3-benzoyl-α-(methylthio)benzeneacetamide (83.2 mmol; obtained in Example 3) were dissolved in a mixture of 330 mL of THF and 80 mL of water and the resulting solution was added in one portion through the addition funnel. The reaction mixture was vigorously stirred at room temperature for 10 min. The yellow solution was unloaded from the vessel and the catalyst was washed twice with 250 mL of THF. The THF solutions were combined and distilled until a volume of 250 mL. Then, 200 mL of 2-propanol were charged twice and distilled until a remaining volume of 250 mL. The solution was allowed to cool crystallizing a yellow solid which was collected by filtration. The product was dried yielding 18.2 g of yellow crystals in needle-like shape (Yield: 86%).

Figure 5:
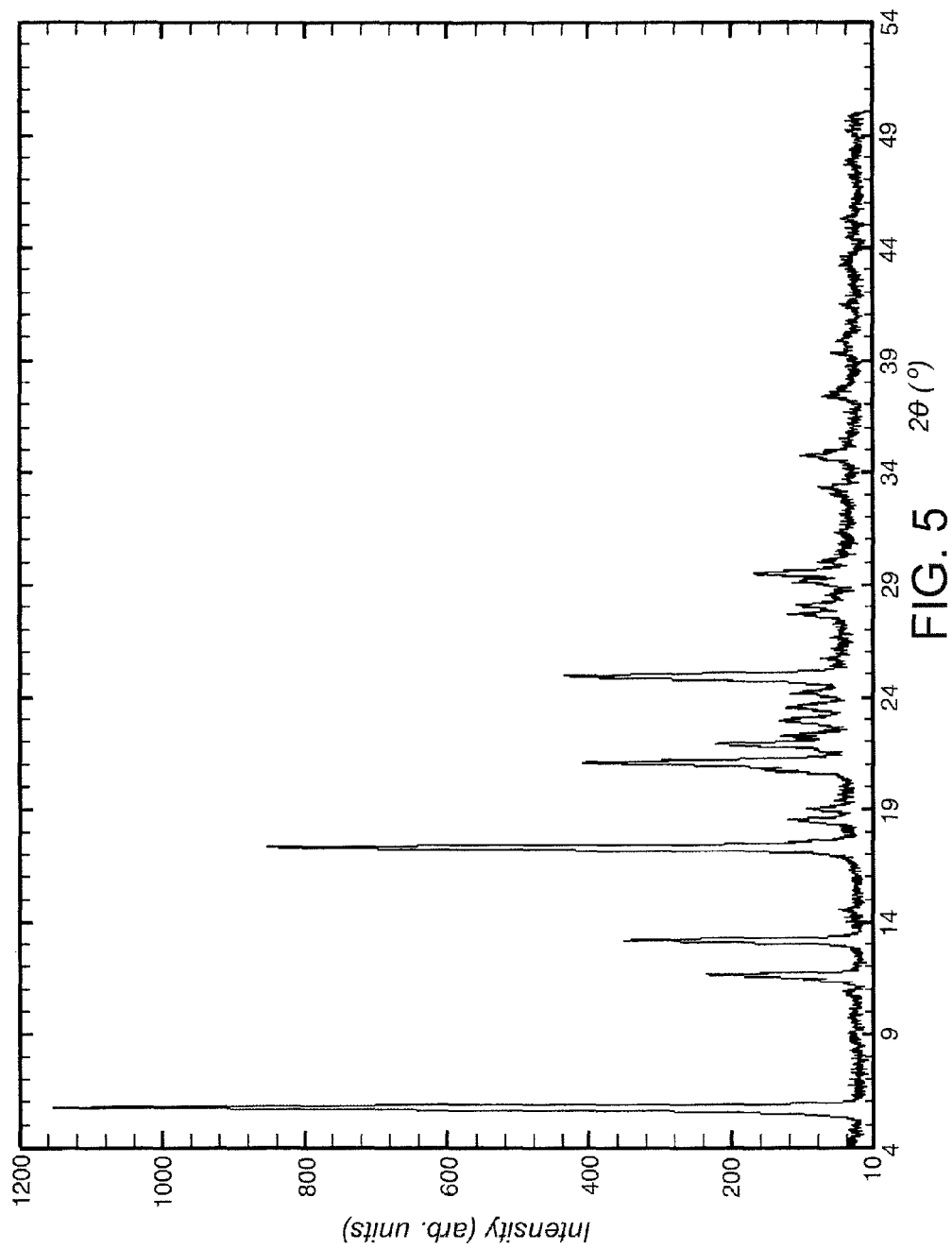
FIG. 5 is an XRD of nepafenac prepared according to an embodiment of the invention.
Figure 6:
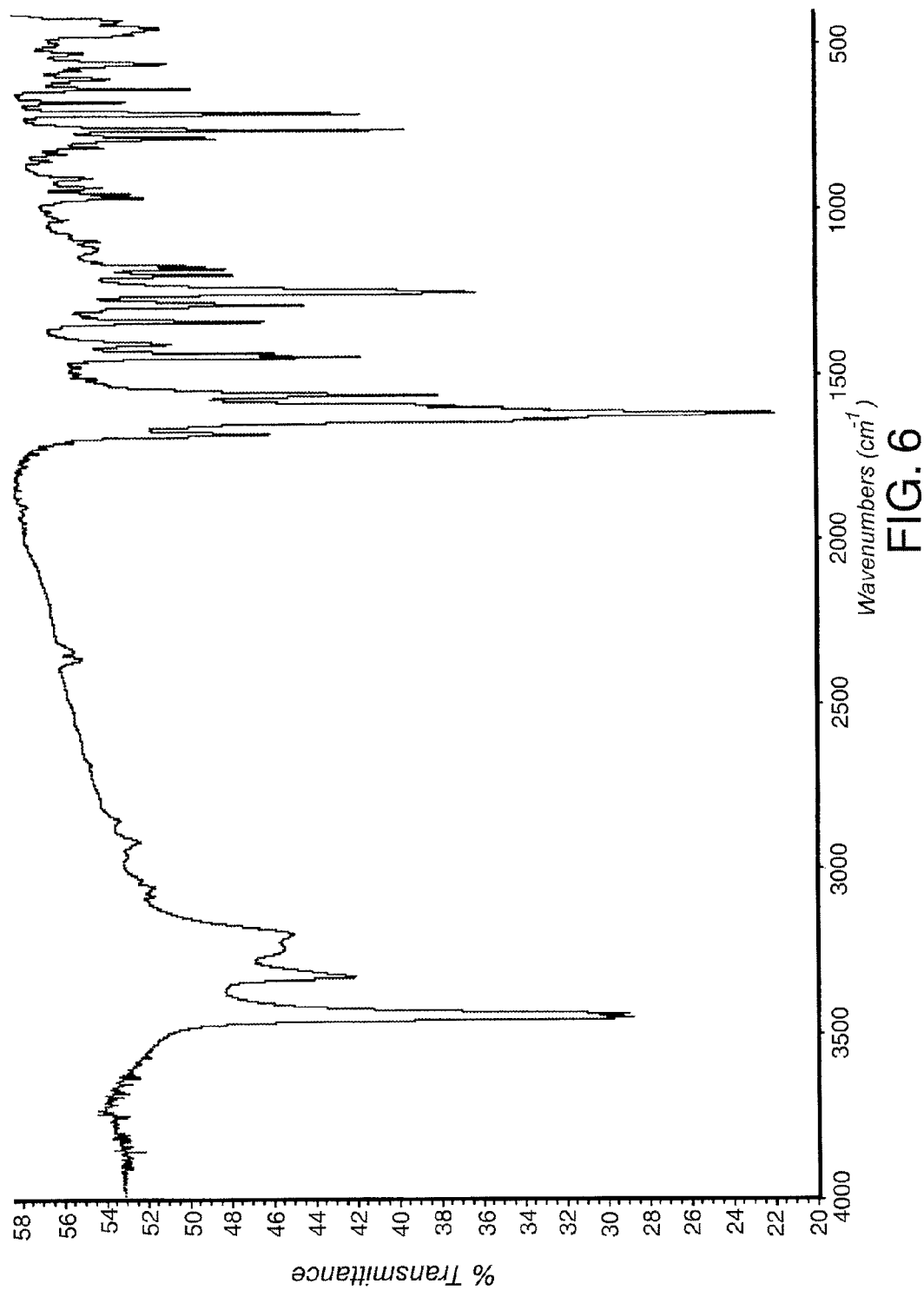
FIG. 6 is an IR spectrum of nepafenac prepared according to an embodiment of the invention.

Analytical data: HPLC purity: 99.6% before the purification, 99.8% after the purification; No chlorination by-products were observed by HPLC; XRD: See FIG. 5; IR: See FIG. 6.

Example 12

Preparation of 2-methylthioacetamide (i.e. compound of formula III)

200 g of methyl(methylthio)acetate were added dropwise over 462.9 g (514.4 mL) of ammonium hydroxide 28-30% during 15 minutes at 20-25° C. and the resulting solution was stirred during two hours at this temperature (soon after mixing the reagents a white solid started to crystallize). Then the suspension was cooled to 0-5° C. and stirred during 2 hours. The solid was collected by filtration and resuspended in 200 mL of 2-propanol at 0-5° C. for 30 minutes. The solid was filtered, washed with 2-propanol and dried at 40° C. under vacuum yielding a white crystalline solid (Yield: 76.2%; GC purity: 99.9%).

Example 13

Preparation of 2-amino-3-benzoyl-α-(2-propylthio) benzeneacetamide

This example illustrates the preparation of a compound of formula (V) using a compound of formula (VI) as a starting material, wherein R is 2-propyl according to an embodiment of the invention.

4.4 g (22.5 mmol) of 2-aminobenzophenone and 3.0 g (22.5 mmol) of 2-(2-propylthio)acetamide were suspended, under inert atmosphere, in 62 mL of anhydrous acetonitrile. The resulting suspension was cooled to −25° C. and a solution of 3.0 g (22.1 mmol) of N-chlorosuccinimide in 28 mL of acetonitrile was added dropwise at such a rate that the temperature did not exceed −23° C. The reaction mixture was stirred at −25° C. during 30 minutes and it was allowed to warm to 0° C. within 2 h. Then, 3.5 mL (24.8 mmol) of triethylamine were added dropwise maintaining the temperature between 0° C. and 5° C. The resulting solution was allowed to warm to room temperature within 1 h and the solvent was concentrated under vacuum. The oily residue was dissolved in dichloromethane and washed three times with water. The organic phase was dried over sodium sulphate and concentrated to yield 6.6 g of a yellowish solid. (Yield: 89%).

All references, including publications, patent applications, and patents, cited herein are hereby incorporated by reference to the same extent as if each reference were individually and specifically indicated to be incorporated by reference and were set forth in its entirety herein.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A process for preparing a compound of formula V:

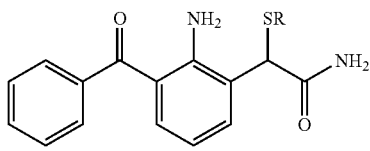

said process comprising
i) reacting a compound of formula (VI):

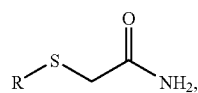

with an N-halosuccinimide compound and 2-aminobenzophenone of formula (II):

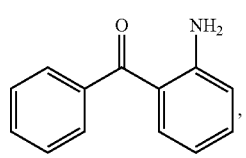

wherein R is an alkyl or aryl group, in the presence of an organic solvent, to obtain a reaction mixture;
ii) treating the reaction mixture with a base to obtain a mixture comprising compound (V), and
iii) optionally, isolating a compound (V) from the mixture.

2. The process of claim 1, wherein the N-halosuccinimide is N-chlorosuccinimide.

3. The process of claim 1, wherein R is methyl, 1-propyl, 2-propyl, or phenyl.

4. The process of claim 1, wherein the compound (VI) is methylthioacetamide and the compound (V) is 2-amino-3-benzoyl-α-(methylthio)-benzeneacetamide.

5. The process of claim 1, wherein the organic solvent is anhydrous.

6. The process of claim 1, wherein the organic solvent of step i) is acetonitrile or dichloromethane.

7. The process of claim 1, wherein the base of step ii) is an organic base.

8. The process of claim 7, wherein the organic base is a trialkylamine or an aryldialkylamine.

9. The process of claim 8, wherein the organic base is a trialkylamine.

10. The process of claim 9, wherein the trialkylamine is triethylamine.

11. The process of claim 4, wherein the organic solvent of step i) is dichloromethane, and the compound (V) isolated in step iii) is compound (IV) in polymorphic Form A:

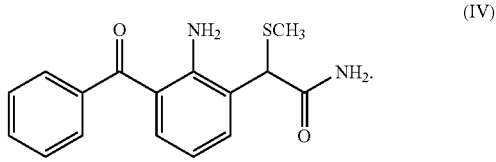

12. The process of claim 4, wherein the organic solvent of step i) is acetonitrile, and the mixture comprising compound (V) of step ii) is a suspension comprising compound (V) wherein said compound V is characterized by an X-ray powder diffraction pattern (2θ) having characteristic peaks at approximately 4.2, 4.8, 5.9, 6.8, 7.9, 10.4, 11.3, 12.5, 13.7, 13.9, 14.4, 15.4, 16.7, 17.2, 17.7, 18.5, 19.2, 19.6, 20.1, 20.6, 21.3, 21.5, 22.2, 23.4, 24.0, 25.1, 25.7, 26.3, 26.9, 27.5, 29.5, 30.1, 32.6, 34.3, 35.8, and 37.8 degrees 2θ (±0.2 degrees).

13. Compound of formula (IV) polymorphic Form B:

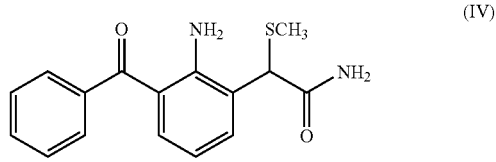

having an X-ray powder diffraction pattern (2θ) having characteristic peaks at approximately 4.2, 4.8, 5.9, 6.8, 7.9, 10.4, 11.3, 12.5, 13.7, 13.9, 14.4, 15.4, 16.7, 17.2, 17.7, 18.5, 19.2, 19.6, 20.1, 20.6, 21.3, 21.5, 22.2, 23.4, 24.0, 25.1, 25.7, 26.3, 26.9, 27.5, 29.5, 30.1, 32.6, 34.3, 35.8, and 37.8 degrees 2θ (±0.2 degrees).

14. The process of claim 12, which produces a compound of formula (V) in polymorphic Form B.

15. A process for preparing compound of formula (IV) polymorphic Form B:

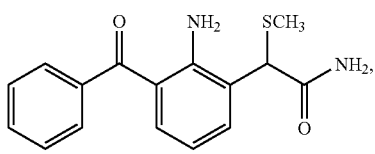 (IV)

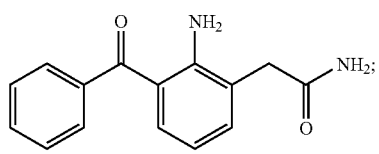 (I)

said process comprising
- i) crystallizing compound of formula (IV) in a solvent comprising methyl isobutyl ketone to obtain a suspension, and
- ii) removing the solvent from the suspension.

16. The process claim 1, said process further comprising:
- iv) reacting a compound of formula (V), with Raney nickel in the presence of a solvent, thereby obtaining a mixture comprising 2-amino-3-benzoylbenzeneacetamide (nepafenac) of formula (I):
- v) isolating nepafenac from the mixture;
- vi) optionally, recrystallizing nepafenac;
- vii) optionally, treating nepafenac with at least one metal scavenger; and
- viii) optionally, reducing particle size of nepafenac.

17. The process of claim 16, wherein step v) is performed in a filter reactor.

18. The process of claim 16, wherein the solvent of step iv) is tetrahydrofuran or a mixture of tetrahydrofuran and water.

* * * * *